(12) United States Patent
Rape et al.

(10) Patent No.: US 12,239,810 B2
(45) Date of Patent: Mar. 4, 2025

(54) WEARABLE APPARATUS CONTAINING A DIGITALLY CONTROLLED DEGRADEABLE MICRONEEDLE ARRAY FOR INTRADERMAL DRUG DELIVERY

(71) Applicant: Lifeware Labs, LLC, Pittsburgh, PA (US)

(72) Inventors: Andrew Rape, Pittsburgh, PA (US); Alexandros Charalambides, Pittsburgh, PA (US); Brian Stancil, Pittsburgh, PA (US)

(73) Assignee: Lifeware Labs, LLC, Pittsburgh, PA (US)

( * ) Notice: Subject to any disclaimer, the term of this patent is extended or adjusted under 35 U.S.C. 154(b) by 1105 days.

(21) Appl. No.: 17/006,112

(22) Filed: Aug. 28, 2020

(65) Prior Publication Data

US 2021/0060323 A1    Mar. 4, 2021

Related U.S. Application Data

(60) Provisional application No. 62/892,632, filed on Aug. 28, 2019.

(51) Int. Cl.
*A61M 37/00* (2006.01)

(52) U.S. Cl.
CPC . *A61M 37/0015* (2013.01); *A61M 2037/0023* (2013.01); *A61M 2205/36* (2013.01); *A61M 2205/50* (2013.01); *A61M 2205/8206* (2013.01); *A61M 2230/04* (2013.01); *A61M 2230/20* (2013.01); *A61M 2230/30* (2013.01); *A61M 2230/42* (2013.01); *A61M 2230/50* (2013.01)

(58) Field of Classification Search
CPC ...... A61M 37/0015; A61M 2037/0023; A61M 2205/36; A61M 2205/50; A61M 2205/8206; A61M 2230/04; A61M 2230/20; A61M 2230/30
USPC ........................................................ 604/506
See application file for complete search history.

(56) References Cited

U.S. PATENT DOCUMENTS

2015/0018755 A1*    1/2015    Chen ................... A61K 9/0021
                                                                    604/46

\* cited by examiner

*Primary Examiner* — Phillip A Gray
(74) *Attorney, Agent, or Firm* — Michael G. Monyok

(57) ABSTRACT

A drug delivery device having an array of solid microneedles embedded with drugs and a light-to-heat-transducing (LTHT) element and a flexible printed circuit board containing a light source, such as a light emitting diode, which can be activated to release the drug embedded in the microneedles through localized melting. The device is worn in contact with the skin of a user, which enables the microneedles penetrate the upper layers of the user's skin. Although in contact with a user's skin, the drugs are not delivered until the device is activated. Activation can occur by an external signal received by the device or through a signal based on a physiological state of the user determined through a sensor in a closed-loop control system.

17 Claims, 5 Drawing Sheets

WEARABLE APPARATUS CONTAINING A DIGITALLY CONTROLLED DEGRADEABLE MICRONEEDLE ARRAY FOR INTRADERMAL DRUG DELIVERY

CROSS-REFERENCE TO RELATED APPLICATIONS

This application claims the benefit under 35 U.S.C. § 119 of U.S. Provisional Application No. 62/892,632, filed Aug. 28, 2019, which is incorporated herein by reference.

STATEMENT REGARDING FEDERALLY SPONSORED RESEARCH

This invention was made with government support under contract number W911QY19P0086 awarded by Medical Countermeasure Systems, United States Army. The government has certain rights in the invention.

BACKGROUND OF THE INVENTION

Intradermal delivery of therapeutic interventions has many advantages over current state-of-the-art drug delivery systems (e.g. intravenous or intramuscular injection, nasal spray, or oral) including ease of administration, lack of pain, and lower drug payload requirements due to the lack of systemic clearance. Microneedles can be used for intradermal drug delivery and overcome some of the drawbacks associated with traditional drug delivery systems. Microneedles are sub-millimeter sized needles that serve to puncture the stratum corneum and epidermis of the skin, which results in an increase in efficiency of intradermal delivery by allowing a direct path to deliver drugs to the dermal microvasculature. Current iterations of microneedle technology include hollow microneedles that serve as conduits for a drug-containing liquid to flow from an external reservoir to the dermal space in the skin and drug-loaded microneedles that degrade when brought into contact with the skin initiating device activation and drug release, typically via dissolution of the constituent parts of the microneedle.

While microneedles represent an exciting technique to deliver drugs intradermally, their practical deployment to clinically relevant scenarios can be accelerated by adding engineering controls that enable a digital interface to specify the precise timing, dosage, and profile of a therapeutic intervention. Such control would enable a microneedle device to be activated remotely by trained medical personnel or it would allow the device to interface with sensors that monitors physiological properties of the user, resulting in closed-loop human-free activation of the system in response to observable health metrics.

BRIEF SUMMARY

The drug delivery apparatus, or patch, according to one embodiment comprises 1) an array of solid microneedles embedded with drugs and a light-to-heat-transducing (LTHT) element; 2) a microelectronics populated flexible printed circuit board (fPCB) containing a light emitting element such as an infrared (IR) light emitting diode (LED) encased in a protective polymer; and 3) an attachment mechanism to attach the microneedle array to the protective polymer, and 4) a separate attachment mechanism to attach the apparatus to the human body. In some embodiments, the apparatus is placed on the human body using a medical grade adhesive as the attachment mechanism and the apparatus is then activated via a digitally controlled wireless signal. When in contact with a user, the microneedles penetrate the upper layers of the user's skin, but the drugs are not delivered until the device is activated. The digital signal turns on the light emitting element to a controlled intensity, which in turn is converted to heat by the LTHT element embedded within the microneedles. This heating results in the localized melting of microneedles. Once the microneedles are in a liquid state, the drug contained within each melted microneedle is able to diffuse into the surrounding tissue and therefore be delivered into the user's blood stream. The location, duty cycle, and intensity of each activated light emitting element results in the ability to precisely control the amount of drug delivered into the surrounding tissue. The microneedles are highly stable and do not dissolve without heat activation, which allows drug delivery to be programmed at specified intervals over a long duration of time. Additionally, embodiments described herein can contain multiple populations of microneedles; specifically, the different populations of microneedles are defined by the activation wavelength of the LTHTs and specific drug contained within each microneedle. The degradation of these different populations can be accessed via distinct wavelengths of lights, which can result in the independent control of the release of multiple drugs from a single, wearable device.

DETAILED DESCRIPTION

Figure 1:
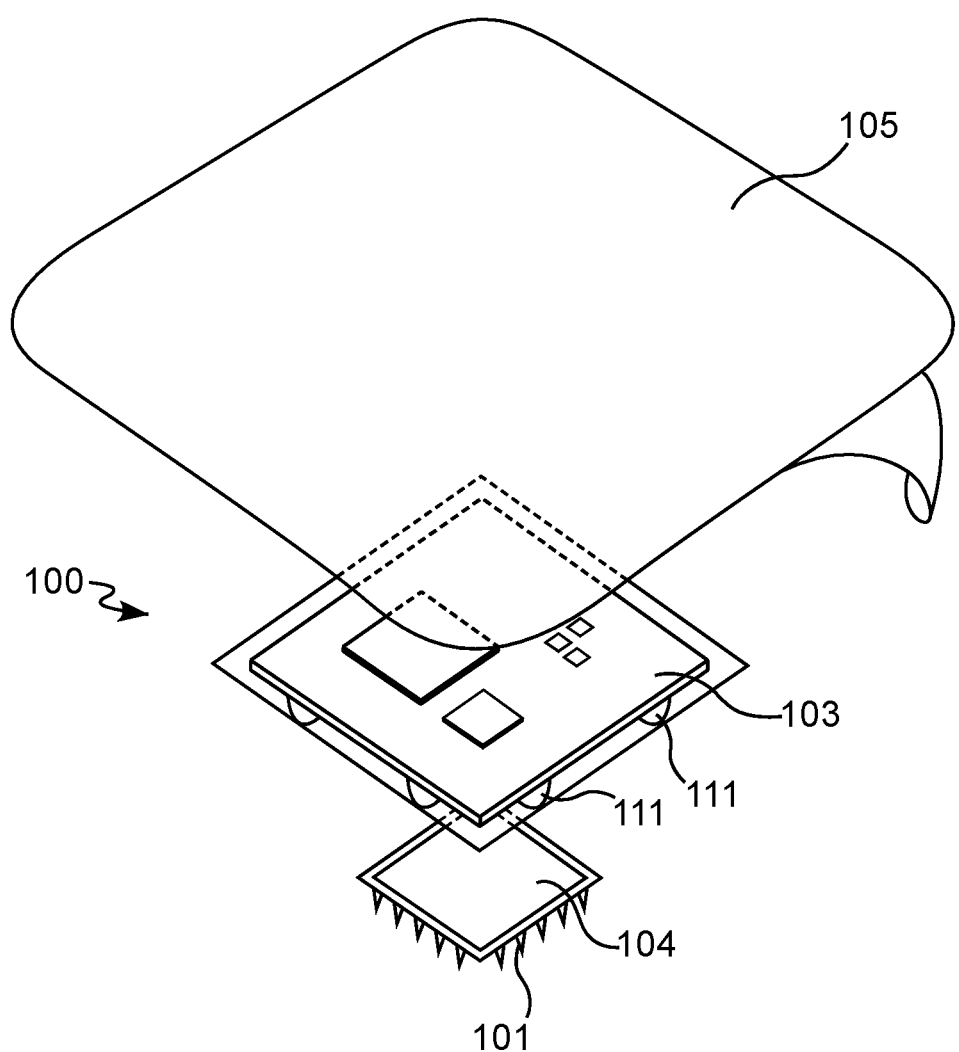
FIG. 1 shows a wearable device having a microneedle array, according to one embodiment.
Figure 2:
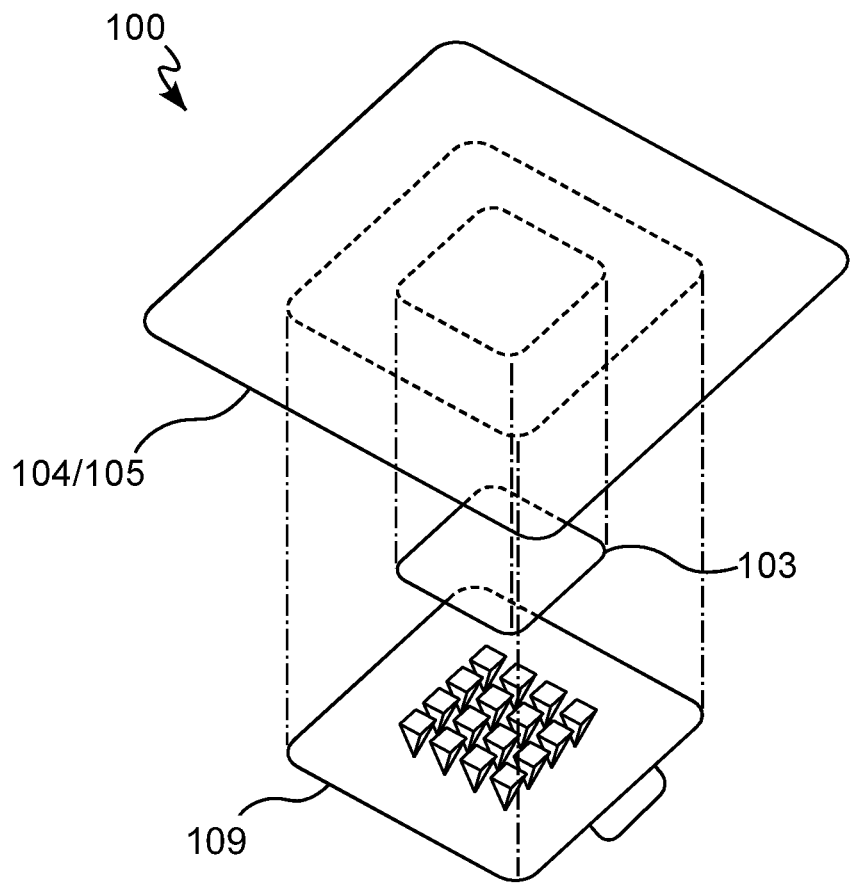
FIG. 2 depicts an alternative embodiment of the wearable device having a microneedle array with a cellulose backing layer.

In one example embodiment, the wearable device 100 comprises 1) a microneedle array 101 that may contain one or more drugs and one or more types of light-to-heat-transducing elements 110 and is attached to a cellulose substrate or backing layer 109, 2) a polymer-encased fPCB 103 with components such as a battery, microprocessor, radio, MOSFETs, light source (e.g. LED, laser, OLED, etc.) 111, and other surface mount electronics, and 3) a means 104 to bond the microneedle array 101 to the device 100 and 4) a second means 105 to attach the device 100 to the skin of a user. In the embodiment shown in FIG. 1, the microneedle array 101 is attached to a surface of the fPCB 103, but other attachment locations may be used. The attachment means 105 is shown in FIG. 1 as an adhesive. Alternatively, the device 100 may use a single adhesive to provide component integration and skin attachment (i.e. combined attachment means 104 and 105), as shown in FIG. 2.

Figure 3A:
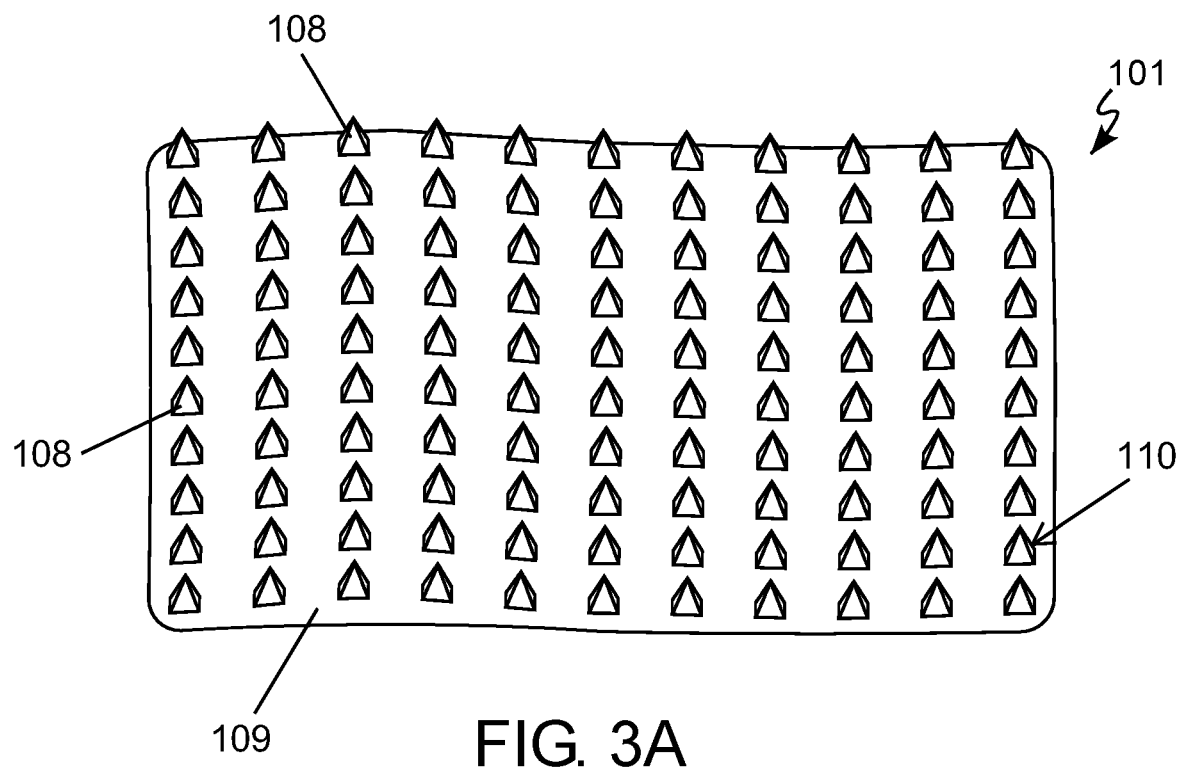
FIGS. 3A-3B show details of the microneedle array and light activation system.
Figure 3B:
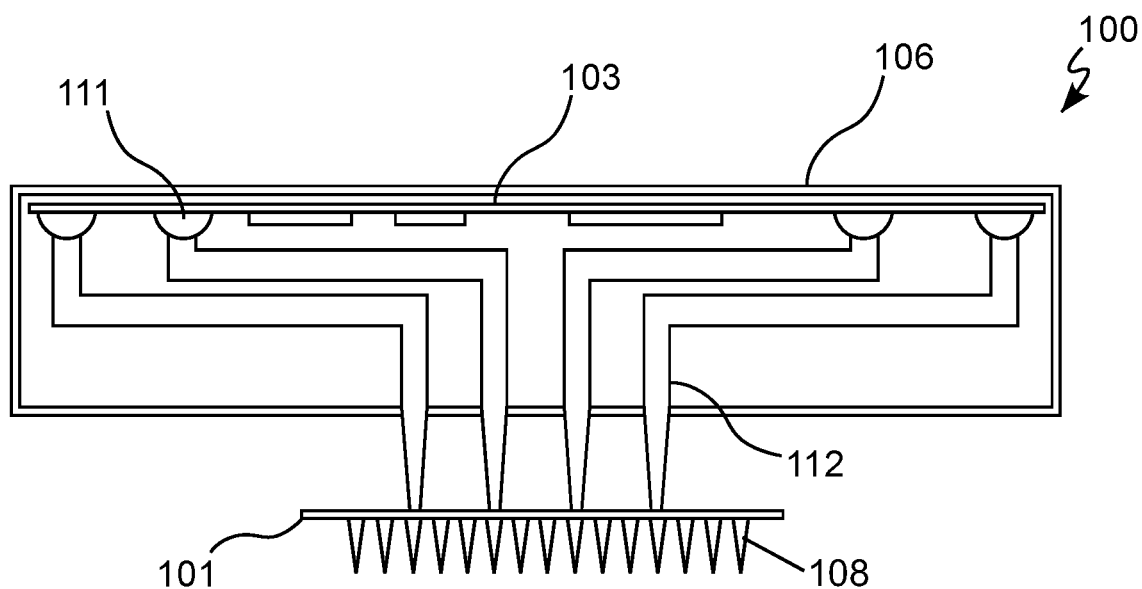

The microneedle array 101 comprises a plurality of individual microneedles 108 that can be connected by an integrated backing layer 109, as shown in FIG. 3. Alternatively, as will be discussed in greater detail, the backing layer 109 can be a separate component affixed to the microneedles 108 during the fabrication process. In some applications, the backing layer 109 is flexible. In yet another alternative embodiment, the array 101 comprises individual microneedles that are integrated with the device 100 without the use of a backing layer 109. In the embodiment shown in FIGS. 1-2, the microneedle array 101 is formed by a casting procedure of a solution of a pre-polymer, the drug intended to be delivered by the device 100, and LTHTs 110. In some embodiments, the prepolymer consists of a predetermined ratio of polycaprolactone (PCL) and a plasticizer, such as ethylene carbonate or trimethyl carbonate. The specific ratio of these constituent components determines the melting point (MP) of the microneedle array 101 and can be altered based on the requirements of the environment for microneedle end-use. For example, the prepolymer can be tuned to melt at 50 C which is sufficiently high to prevent accidental melting even in high temperature environments, but low enough to be activated via infrared light. In this example embodiment, a ratio of 5:1 of PCL to ethylene carbonate yields a final melting point of approximately 48-50 C. Because of the small size of the microneedles 108 in the array 101, elevated temperatures can be used without causing tissue damage.

As part of the casting process, PCL, with or without plasticizer, is dissolved in acetone and mixed with LTHTs 110 such as gold nanorods. In this example embodiment, gold nanorods are used as the LTHTs 110 because they efficiently absorb infrared light and can be tuned to a specific wavelength. However, other metals or non-tunable filler materials, such as carbon black, can be used as the LTHTs 110. While acetone is used in this example embodiment, other solvents that (1) dissolve PCL and (2) are miscible in water can be used with water soluble drugs. For drugs that are soluble in organic solvents, the solvent should: (1) dissolve PCL and (2) be miscible with other organic solvents. A potential example of a solvent in this system would be chloroform or dichloromethane. In the case of gold nanorods, the length of the nanorods tailors the wavelength of light that induces heating. A separate solution of drug is prepared in a solvent that is miscible with acetone and is subsequently mixed thoroughly into the PCL/plasticizer/LTHT solution. This solution is cast into an elastomeric mold that is the negative mold of the desired microneedle array 101, and is held at a temperature above the melting point (MP) of the PCL/plasticizer mixture, resulting in the evaporation of all acetone from the mixture. Migration of the solution into the cavities of the negative mold can be accomplished via gravity-, vacuum-, or centrifugal-based procedures. The resulting liquid microneedles 108 are then brought into manual contact with a thin cellulose-based backing layer 109 and forced to cool slowly via an oven whose temperature is slowly decreased to room temperature. The force slow cooling process improves the consistency in the melting point of individual microneedles 108. After solidification of the microneedles 108 and backing layer 109 (if present), they are removed from the elastomeric mold, resulting in an array 101 of solid microneedles containing a drug and LTHTs 110.

The negative mold previously described can be manufactured via a 3D printed positive mold, followed by casting silicone such as Dow Corning Sylgard 184 that is peeled away after curing. However, a person having skill in the art will understand that a mold can be fabricated by a variety of methods.

A flexible printed circuit board 103 is manufactured containing components such as a battery, microprocessor or microcontroller, radio, MOSFETs, a light source 111, such as LEDs, and other surface mount electronics. While a flexible printed circuit board 103 can allow the device 100 to be more comfortably worn by a user, a solid circuit board or a flexible board containing several non-flexible components with flexible interconnects can be used. In one embodiment, the microcontroller is wirelessly paired to a tablet or cell phone via a protocol such as Bluetooth. The user of the device 100 can select and/or define a specific dosage protocol (including but not limited to: rate of drug release, time of drug release, frequency of drug release, and number of cycles of drug release), which is transmitted to the Bluetooth-enabled microcontroller. The microcontroller processes this protocol and activates specific LEDs 111 for prescribed periods of times and intensities. Possible drug release protocols include one-time bolus delivery, multiple bolus deliveries at a specified frequency for a specified duration of time, or continuous diffusion protocols that could potentially vary the rate of drug delivery as a function of time.

Light emitted from LEDs 111 can be controlled via coupling to flexible polymers of defined shapes with refractive indexes different than the refractive index of air. These polymer-based light guides 112, such as an optical waveguide, light tube, lens, optical fiber, Fresnel lens, etc., can be used to direct light more efficiently onto specific areas of the microneedle array 101, as shown in FIG. 3. Additionally, incorporation of light guides 112 into the device 100 enable the physical dissociation of LED 111 location and microneedle array 101 location, which can enable enhanced LED 111 thermal management strategies and more desirable device 100 form factors. In one embodiment, the light guide 112 comprises a polymer-based optical fiber; however, a person having skill in the art will appreciate that other materials or structures can be used to guide the light emitted from the light source 111 to the light-to-heat transducing element 110 containing within the microneedle 108.

Figure 4:
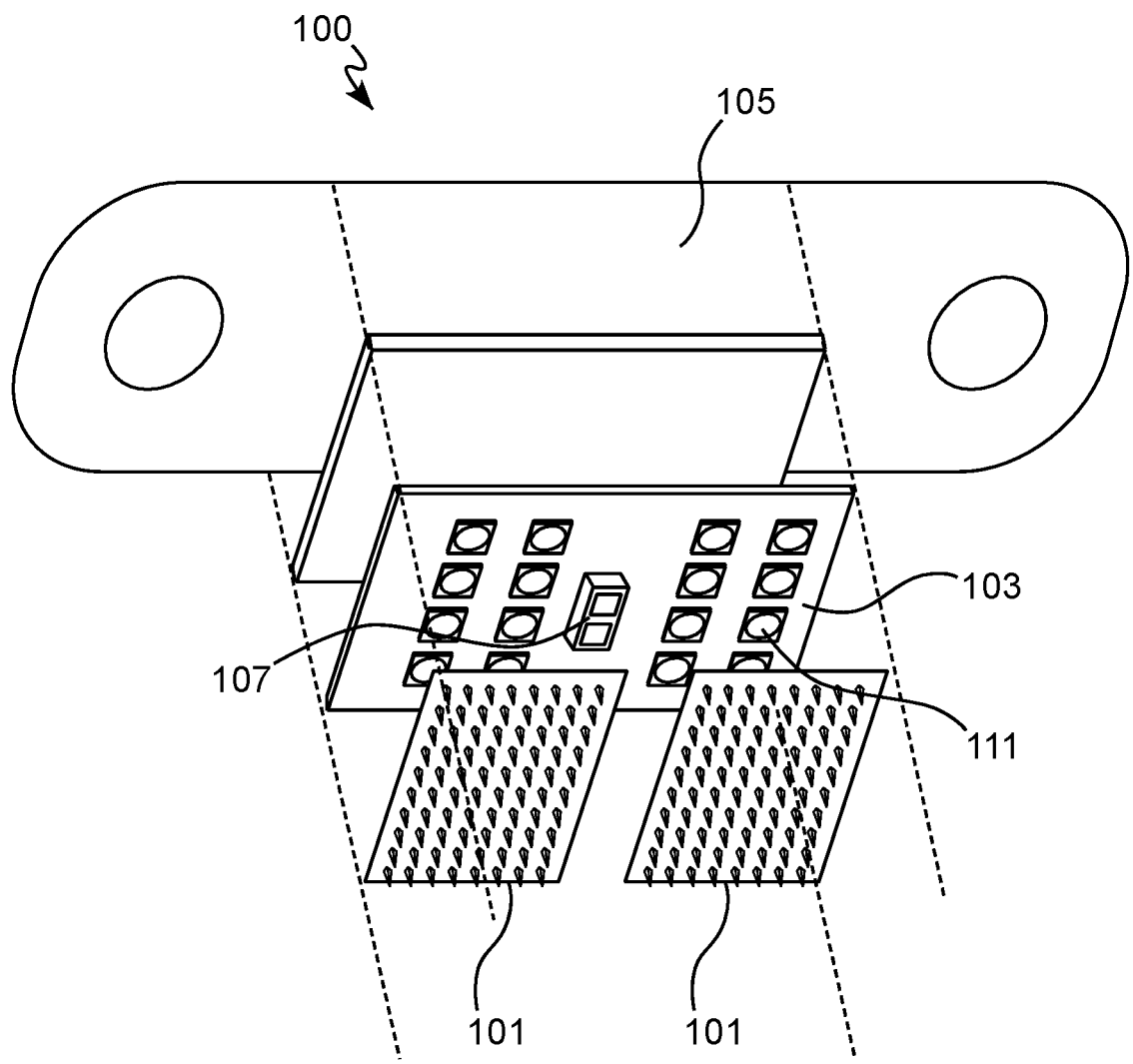
FIG. 4 is a diagram of an alternative embodiment having multiple populations of microneedles.

The foregoing examples depict an externally controlled device 100, where the administration of the drug is predetermined based on a timer, a manual activation signal, or some other external signal communicated to the controller. Alternatively, a closed-loop sensing and delivery system can be implemented in which physiological data such as electrocardiogram, pulse oximetry, respiratory rate, body temperature, and blood pressure can be monitored and used to assess the need to deliver a drug to the body automatically. Stated differently, administration of the drug is dependent on the user's physiological state, which can be sensed by the device 100. In this configuration, the device 100 is connected to a sensor 107 or a series of physiological sensors 107, either co-located on the apparatus 100 itself or externally but connected either with flexible wires or wirelessly, and specific measured physiological states would trigger the apparatus 100 to deliver a drug. For example, to treat opioid exposure the microneedles 108 could be loaded with a drug such as naloxone hydrochloride, and physiological states such as low respiratory rate, low blood pressure, low blood oxygenation, and a dramatic change in heart rate could be used to automatically trigger the LEDs 111, melt the microneedles 108, and administer the drug. An example embodiment of the microneedle array 101 with physiological sensors 107 within the apparatus itself can be seen in FIG. 4.

In one embodiment, the microneedle array 101 can be bonded to the polymer-encased fPCB 103 via a double-sided medical grade adhesive 104. Most adhesives demonstrate good bonding to cellulose material, but satisfactory-to-poor adhesion to polymers. The adhesion to the polymer can be dramatically improved by an oxygen plasma treatment minutes prior to mating and bonding the polymer device and adhesive surfaces. Lastly, an attachment means 105, such as an adhesive, that attaches the device 100 to the human skin is placed over the device 100, and the release liner may be removed when ready to be applied to the body. Other attachment means 105 may be used, such as a strap or direct suturing.

In an alternative embodiment, the device 100 is designed to enable radiation transparency. In this embodiment, a polymer encasing the fPCB 103, the adhesive 104 connecting the microneedle array 101 to the fPCB 103, and the cellulose substrate 109 for the microneedle array 101 must be transparent with respect to the wavelength of light used to activate the microneedle array 101, so that light from the fPCB 103 can reach the microneedle array 101.

Figure 5:
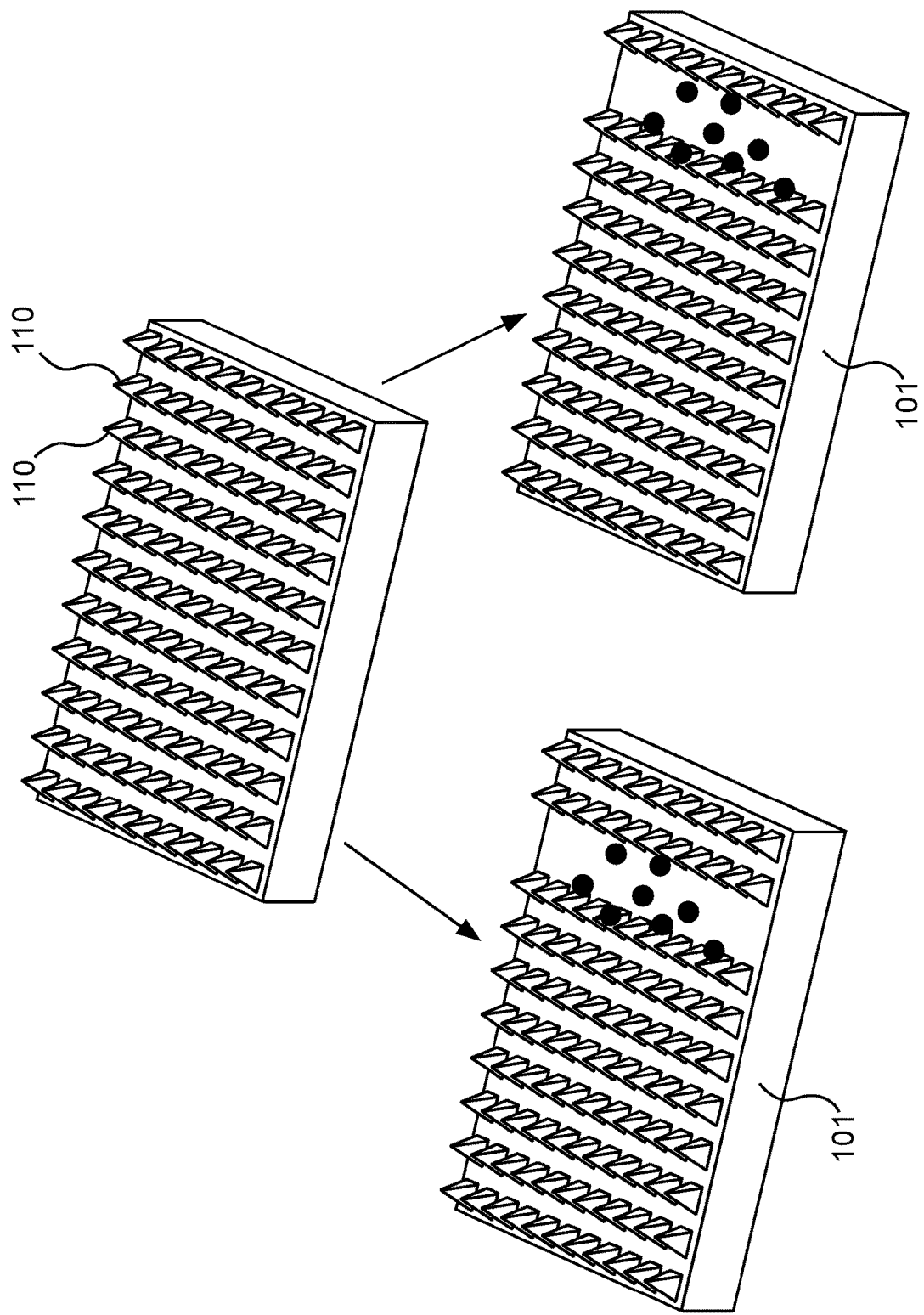
FIG. 5 is another alternative embodiment with LED's having different wavelengths.

In some embodiments, more than one drug can be embedded in the microneedle array 101. To accomplish this, the microneedle array 101 can contain multiple populations of distinct microneedles 108 that are defined by the activation wavelength of the LTHT 110 and the type of drug contained within them. If the activation wavelength band of each LTHT 110 is sufficiently narrow and well-separated from the activation bands of all other populations of microneedles 108, degradation of each population of microneedle 108 can be achieved by exposing the entire microneedle array 101, or a portion of it, to light corresponding the specific activation wavelength of the desired population to be degraded, as shown in FIG. 5. As shown in FIG. 5, a first row or a second row of microneedles 108 can be activated to release a drug independently of the other. The circuit board 103 would also need to include multiple LEDs 111 that emit various wavelengths of light to activate each microneedle population. For example, in one embodiment the device 100 contains multiple populations of microneedles 108 with non-overlapping absorption spectra, where one population contains gold nanorods with an absorption peak at ~800 nm and another population with an absorption peak at 1064 nm. The absorption spectra can be tailored to a range of wavelengths by altering the aspect ratio of the gold nanorod used as the LTHT 110.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof. In particular, one or more features in any of the embodiments described herein may be combined with one or more features from any other embodiments described herein.

Protection may also be sought for any features disclosed in any one or more published documents referred to and/or incorporated by reference in combination with the present disclosure.

What is claimed is:

1. A wearable device for intradermal delivery of a drug comprising:
 a microneedle array comprising a plurality of microneedles,
  wherein each microneedle of the microneedle array comprises the drug, a light-to-heat transducing element, and a polymer;
 at least one light source comprising a light emitting diode; and
 a controller to operate the at least one light source,
 wherein light energy emitted from the at least one light source is absorbed by the light-to-heat transducing element, causing a rise in temperature that melts the polymer and releasing the drug.

2. The wearable device of claim 1, wherein the light-to-heat transducing element comprises a gold nanorod.

3. The wearable device of claim 1, further comprising: an attachment means to affix the device to a user's skin.

4. The wearable device of claim 1, further comprising a cellulose substrate attached to a surface of the microneedle array.

5. The wearable device of claim 3, wherein the attachment means comprises an adhesive.

6. The wearable device of claim 1, further comprising:
 a light guide selected from the group consisting of an optical waveguide, a lens, and an optical fiber,
 wherein the light guide directs light emanating from the light source to at least one microneedle of the microneedle array.

7. The wearable device of claim 1, wherein the polymer has a melting point of about 48-50 C.

8. The wearable device of claim 1, wherein the controller activates the light source based on a signal received by the controller from an external source.

9. The wearable device of claim 1, wherein the controller activates the light source based on a signal originating within the controller.

10. The wearable device of claim 1, further comprising:
 a sensor capable of providing data related to a physiological state of the user.

11. The wearable device of claim 10, wherein the physiological state is selected from the group consisting of an electrocardiogram, pulse oximetry, respiratory rate, body temperature, and blood pressure.

12. The wearable device of claim 10, wherein the controller activates the light source based on the physiological data.

13. The device of claim 10, wherein the sensor is located on the device.

14. The device of claim 10, wherein the sensor communicates directly with the controller.

15. The device of claim 1, wherein a first light source activates a first population of microneedles and a second light source activates a second population of microneedles.

16. The device of claim 15, wherein the first population and the second population have light-to-heat transducing elements that respond to different frequencies of light.

17. A method of intradermally delivering a drug using a wearable device, the method comprising:
 affixing a wearable device to a user's skin, wherein the device comprises:
  a microneedle array comprising a plurality of microneedles,
   wherein each microneedle of the microneedle array comprises the drug, a light-to-heat transducing element, and a polymer;
  at least one light source comprising a light emitting diode; and
  a controller to operate the at least one light source,
 activating the at least one light source, wherein light energy emitted from the at least one light source is absorbed by the light-to-heat transducing element, causing a rise in temperature that melts the polymer and releasing the drug.

* * * * *